United States Patent [19]

Korte et al.

[11] Patent Number: 5,286,896
[45] Date of Patent: Feb. 15, 1994

[54] PROCESS FOR THE PRODUCTION OF DMT-INTERMEDIATE PRODUCT OF SPECIFIC PURITY

[75] Inventors: Hermann-Josef Korte, Niederkassel; Anton Miletic, Troisdorf; Hans U. Neutzler, Wetter; Anton Schoengen, Witten; Johann H. Schroeder, Dortmund; Ralf Wirges, Niederkassel, all of Fed. Rep. of Germany

[73] Assignee: Hüls Aktiengesellschaft, Marl, Fed. Rep. of Germany

[21] Appl. No.: 761,768

[22] PCT Filed: Feb. 13, 1990

[86] PCT No.: PCT/EP90/00230

§ 371 Date: Aug. 15, 1991

§ 102(e) Date: Aug. 15, 1991

[87] PCT Pub. No.: WO90/09367

PCT Pub. Date: Aug. 23, 1990

[30] Foreign Application Priority Data

Feb. 16, 1989 [DE] Fed. Rep. of Germany ....... 3904586

[51] Int. Cl.$^5$ ............................................. C07C 67/39
[52] U.S. Cl. .................................. 560/77; 562/483
[58] Field of Search ...................... 560/77; 562/483

[56] References Cited

U.S. PATENT DOCUMENTS

| | | | |
|---|---|---|---|
| 3,914,287 | 10/1975 | Takeda et al. | 560/77 |
| 4,092,481 | 5/1978 | Bunger | 560/77 |
| 4,096,340 | 6/1978 | Fujii et al. | 560/77 |
| 4,126,755 | 11/1978 | Bunger et al. | 560/77 |
| 4,342,876 | 8/1982 | Klingmann | 560/77 |

FOREIGN PATENT DOCUMENTS 3044617 9/1985 Fed. Rep. of Germany.

*Primary Examiner*—Jose' G. Dees
*Assistant Examiner*—Vera C. Clarke
*Attorney, Agent, or Firm*—Millen, White, Zelano, & Branigan

[57] ABSTRACT

The invention relates to a process for the production of a DMT intermediate product as well as its working up to fibregrade DMT and to medium pure and pure terephthalic acid. The DMT intermediate product is moreover produced by combined oxidation of a predominantly para-xylene (p-X) and para-toluic acid methyl ester (p-TE) containing mixture in liquid phase with an oxygen containing gas, esterification of the acids being produced with methanol, distillative or rectificative separation of the esterification products being produced into a p-TE rich fraction I, a fraction II containing more than 99% by weight DMT and its isomers and a high boiling residue fraction III as well as feeding back the p-TE fraction I into the oxidation, with the residue fraction III having a DMT content of 15 to 70% by weight and the DMT fraction II being purified by single solvent recrystallisation in methanol to form the DMT intermediate product to such an extent that the amounts of hydroxymethylbenzoic acid methyl ester (HM-BME) and terephthalic acid methyl ester (TAE) in the DMT intermediate product amount together to less than 200 ppm.

9 Claims, 6 Drawing Sheets

PROCESS FOR THE PRODUCTION OF DMT-INTERMEDIATE PRODUCT OF SPECIFIC PURITY

FIELD OF THE INVENTION

The invention relates to a process for the production of DMT-intermediate product according to the preamble of claim 1 as well as its working up to medium pure or fibregrade dimethylterephthalate (DMT-p) and/or medium pure or pure terephthalic acid (MTA/PTA).

Dimethylterephthalate (DMT) is produced in numerous large scale plants according to the so-called Witten-DMT-Process (cf. German Patent Specification 10 41 945). DMT is subsequently worked up to polyesters by reaction with multifunctional alcohols. Those high molecular compounds—also known as saturated polyesters—are worked up inter alia to form fibres, filaments, films or moulded parts.

STATE OF THE ART

According to the Witten-DMT-Process, a mixture of para-xylene (p-X) and para-toluic acid methylester (p-TE) is oxidised in the liquid phase in the absence of solvents and of halogen compounds at a pressure of about 4 to 8 bar and a temperature of about 140° to 180° C. with atmospheric oxygen in the presence of dissolved heavy metal oxidation catalysts, e.g. in the presence of a mixture of cobalt and manganese compounds (cf. German Patent Specification 20 10 137).

Subsequently to the oxidation step, the reaction mixture obtained, which consists predominantly of monomethyl terephthalate (MMT), p-toluic acid (p-TA) and terephthalic acid (TA), dissolved or suspended, resp., in para-toluic acid methyl ester (pT-ester) and dimethyl terephthalate (DMT), is esterified with methanol at a pressure of 20 to 25 bar and a temperature of about 250° to 280° C. Higher pressures are technically possible but for cost reasons are not used. The esterification product is distillatively separated into a p-TE-fraction, a crude DMT fraction and a high boiling, tar-like residue. The p-TE-fraction is fed back into the oxidation. The high boiling, tar-like distillation residue contains, inter alia, all the constituents of the catalyst system, which according to EP-B-0 053 241 can be recovered and fed back into the oxidation.

The crude DMT originating from the distillation and having a typical purity of 97 to 99.9% contains, besides about 0.05 to 2% of isomers of DMT (dimethylortho- and dimethylisophthalate [DMO, DMI]), still partly interfering amounts of terephthalaldehydic acid-methylester (TAE), monomethylterephthalate (MMT), para-toluic acid (p-TA) and other impurities resulting from the p-xylene employed or from side reactions.

For purification of the crude DMT to pure fibregrade) DMT (DMT-p), with it being necessary in particular, for TAE and the isomers to be removed, it is known to treat the crude DMT by methanolic recrystallisation (German Offenlegungsschrift 20 14 012, Hydrocarbon Processing, Nov. 1983, P. 91). For attaining a purity of the DMT (sum of impurities inclusive of the isomers DMO and DMI less than 100 ppm) sufficient for fibre production (fibregrade DMT), it has been to some extent usual to carry out the recrystallisation twice with intermediate washing with methanol, with the methanol being fed in countercurrent. In addition a final distillation of the DMT has still been necessary hitherto with a crude DMT of low purity.

The filtrate residue obtained in the methanolic recrystallisation by filtration from the mother liquor still contains, in addition to the isomers DMO and DMI, large amounts of DMT and other valuable products (intermediate products in the DMT-process), so that the filtration residue was hitherto as a general rule for the largest part fed back into the oxidation. As a result of this feeding back of filtration residue, the isomers accumulate up to values of 8 to 12% by weight so that the antecedent reactors and especially the distillation and recrystallisation must have additional capacities. The feeding back of the filtration residue was, according to the state of the art, necessary for obtaining sufficiently "neutral products" for the adjustment of the melting point and the acid number in the oxidation and the flowability of the oxidation product to the esterification.

From German Patent Specification 30 11 858 and German Patent Specification 29 16 197 it is known that the amount of terephthalaldehydic acid methylester (TAE) in the DMT intermediate product must be kept as small as possible, in particular in the working up to form fibregrade terephthalic acid (PTA). In German Patent Specification 30 11 858, there is proposed a particularly expensive rectification column, for reduction of the TAE content in the crude DMT, in which column the TAE content in the crude DMT can be reduced to values of <0.01% by weight.

In spite of this high cost, it has been shown with this process that an always still interfering large amount of terephthalaldehydic acid (TAS, 4-CBA), the acid formed from the TAE in the hydrolysis, can be present in the end product, terephthalic acid (TA). The residual content of TAS in the terephthalic acid could then assume in particular inexplicably high values if the crude DMT had to be stored in the meanwhile before the working up to terephthalic acid.

OBJECT OF THE INVENTION

It is the object of the present invention to improve the process of the indicated type for the production of DMT intermediate product to the effect that, in the working up of the DMT intermediate product to fibregrade DMT, the TAE content, and in the working up to PTA, the TAS content, is reduced further. In particular, even with longer intermediate storage of the crude DMT and then working up to pure DMT or PTA respectively, the TAE content or the TAS content, in the end product should be kept as low as possible.

Further concerns of the invention are the lowering of the cost of apparatus and energy in the DMT and PTA production, the increasing of yield and the creation of a possibility of producing DMT-p and PTA simultaneously in one plant.

SUMMARY OF THE INVENTION

This object is solved according to the invention by the features of claim 1.

It is an essential feature of the invention to improve and to simplify the purification of the crude DMT by cost effective rectification and subsequent single solvent recrystallisation.

The largest part of the impurities—with exception of the isomers—is removed according to the invention by rectification so that the thus purified crude DMT (fraction II) preferably has a TAE and hydroxymethyl-benzoic acid methylester content (HM-BME) of together less than 0.2% by weight (2.000 ppm). The rectification of the ester mixture can be simplified, in relation to the process according to German Patent Specification 30 11 858 because the high boiling residue fraction III has a high DMT content of 15 to 70% by weight, preferably 40 to 60% by weight.

Likewise, the p-TE rich fraction I can have a high DMT content, this lying preferably at 20 to 30% by weight.

The residue fraction III can be prepared for example with a process according to German Patent Specification 24 27 875. According to a preferred embodiment of the invention, the residue fraction is however prepared by methanolysis in two steps, with the DMT as well as further valuable products being fed back into the oxidation. In all, the DMT content, which is recovered from the residue fraction and is fed back into the oxidation, amounts preferably to 3 to 7% by weight related to the sum of all the components supplied in the liquid phase to the oxidation.

Preferably, the p-TE fraction I is fed back in excess to the oxidation so that still about 5 to 30% by weight of p-TE, in particular 20 to 25% by weight, are obtained in the acid mixture being produced in the oxidiser.

The adjusted p-TE excess as well as the DMT quantities recycled serve for increasing reaction and for melting point adjustment of the product flow leaving the oxidiser. Melting points of 130° to 150° C. with an acid number of 200 to 300 g KOH/kg oxidate are preferred.

The crude DMT purified by rectification (fraction II) is then subjected to a single solvent recrystallisation, preferably in methanol, in order to remove residual amounts of TAE, HM-BME and other impurities. At the same time, the isomers DMO and DMI can be removed in this step.

According to a preferred embodiment of the invention, the mother liquor originating from the (first) methanolic recrystallisation is concentrated by evaporation of methanol. The dissolved DMT with amounts of isomers and impurities corresponding to the solvent equilibrium are then crystallised out as a result of further cooling to about 20° to 50° C., preferably about 25° C., filtered off and after mixing with methanol fed back to the (first) recrystallisation. The substances still dissolved in the remaining mother liquor, predominantly DMO, DMI and residues of DMT as well as the amounts of TAE and HM-BME not removed in the rectification, are concentrated by evaporation of the residual methanol and discharged as residue from the process or fed back into the oxidation.

Insofar as is usual according to the state of the art, the p-xylene employed has an isomer content of above 1,000 to 5,000 ppm, according to a preferred embodiment of the invention, a feeding back into the oxidation of the residue being deposited is completely dispensed with. A complete discharging of the residue is therefore not subject to uneconomical losses because, in the preceding rectification, the valuable products TAE and HM-BME have already been removed almost completely from the crude DMT. At the same time, a feeding back of residue—in contrast to the known processes—is also not necessary for the adjustment of the melting point and the acid number in the oxidiser since the neutral product quantities needed for this purpose are fed back into the oxidation as DMT-proportions of the p-TE-fraction I and the residue fraction III.

With p-xylene particularly clean with respect to isomers, with isomer amounts below 100 to 500 ppm, the entire residue can optionally also be fed back into the oxidation, insofar as a corresponding amount of isomers can be tolerated in the end product. With these small amounts of isomers in the p-xylene, which according to the present state of the art is certainly not in sufficient amounts for convenience, the amount of residue fed back is however relatively small, amounting to about 3 to 6% by weight of the amount of DMT fed back into the oxidation from the rectification.

Indeed, depending on required end product purity and amount of isomers in the p-xylene, a part of the filtrate residue can also optionally be fed back into the oxidation, with the amount of DMT and its isomers being small in relation to the amounts of DMT, which are fed back into the oxidation from the rectification.

It is a further essential feature of the invention to minimise also the amount of the impurity hydroxymethyl-benzoic acid methylester (HM-BME) present in the DMT intermediate product, in addition to TAE.

It has been surprisingly shown that the amount of HM-BME in the crude DMT, in addition to the amount of TAE, is decisive for the TAE content in the fibregrade DMT or for the amount of TAS in PTA. It is supposed that HM-BME in the intermediate storage tank connected to the DMT production or in the subsequent processing steps is reacted with atmospheric oxygen to form TAE, with the atmospheric oxygen being able to be present in the closed plant as a result of unavoidable micro leakages in the distillation part, which is run with sub-atmospheric pressure. This relationship was unknown until the time of the invention.

As a result of the process according to the invention for the production of DMT intermediate product, it has been possible for the first time to essentially simplify the subsequent processing steps for producing fibregrade DMT and/or PTA, without the TAE content in the pure DMT or the TAS content in PTA assuming higher values. Also, with longer interim storage of the DMT intermediate products, it can be guaranteed reliably that the amount of TAE or TAS in the end product does not increase further, so that a uniform quality is attained.

The DMT intermediate product according to the invention with a typical content of isomers, TAE and HM-BME of, in total, 50 to 200 ppm can be worked up by a second recrystallisation in methanol with low cost in apparatus to fibregrade DMT with a typical purity of >99.995% by weight. The content of impurities may be reduced, when needed, once again to values of <10 ppm by means of an additional methanolic washing of the DMT intermediate product before the final recrystallisation.

The working up of the DMT intermediate product to terephthalic acid takes place preferably by hydrolysis in a simple reactor, the produced methanol being removed together with the by-product dimethylether (DME) by feeding in of stripping steam. The terephthalic acid formed is discharged from the reactor suspended or dissolved in water and crystallised out in multiple stages, centrifuged and dried. Insofar as the DMT intermediate product is supplied to the hydrolysis directly without additional water, the medium pure terephthalic acid (MTA) typically contains 500 to 1,000 ppm of impurities. By means of a simple washing of the DMT intermediate product in methanol and subsequent centrifuging, the purity of the terephthalic acid may be increased to 100 to 150 ppm (PTA), with the impurities chiefly consisting of MMT. As a result of simple washing of the PTA in water, even the MMT content, insofar as necessary, may be further reduced so that a terephthalic acid with a purity hitherto hardly attainable in a large scale industrial plant with a sum of all impurities inclusive of MMT and p-TA of <50 ppm can be produced (PTA-p).

Furthermore, an essential saving of energy is achieved with the process according to the invention. Of especial value is the possibility of working up the DMT intermediate product according to the invention both to fibregrade DMT (DMT-p) and also to medium and pure terephthalic acid (MTA or PTA) with this working up being essentially simplified, for example in comparison to the DMT intermediate product according to German Patent Specification 29 16 197 and German Patent Specification 30 11 858, since the DMT intermediate product according to the invention has only very small residual contents of isomers. Finally, the process according to the invention opens up the possibility of producing terephthalic acid of very high purity (PTA-p) with, in contrast to conventional PTA, reduced amounts of impurities, in particular even of MMT and p-TA.

Of special advantage is finally the possibility of producing with reduced additional cost of apparatus and energy at the same time pure DMT and fibregrade or very high purity terephthalic acid, with the proportions of DMT-p/PTA and PTA-p being able to be varied as desired.

BRIEF DESCRIPTION OF THE DRAWINGS

The process according to the invention is explained in the following by means of explanatory examples as well as the drawings.

There are shown herein as plans for plant.

WAYS OF CARRYING OUT THE INVENTION

EXAMPLE 1

Figure 1:
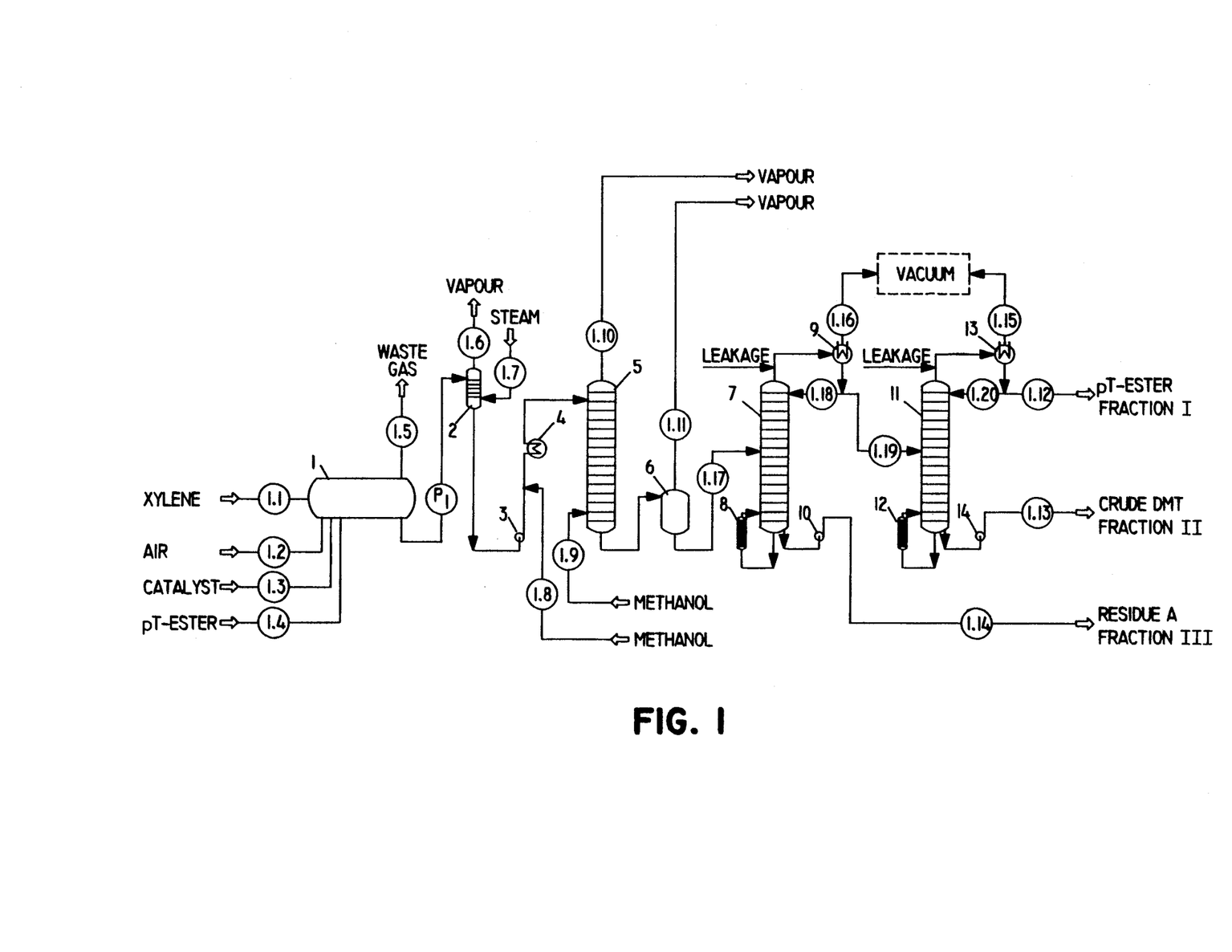
FIG. 1 a plant for the production of crude DMT with oxidiser, esterification column and crude ester rectification, FIG. 2 a plant for residue working up of the sump fraction "Residue A" according to FIG. 1, FIG. 3 a plant for the purifying of the crude DMT fraction from FIG. 1 to form DMT intermediate product and fibregrade DMT, FIG. 4 a plant for the filtrate working up of "Filtrate A" according to FIG. 3, FIG. 5 a plant for the hydrolysis of DMT intermediate product to form PTA, FIG. 6 a plant for the simultaneous production of PTA and PTA-p.

In FIG. 1 there is shown a plant for the production of crude DMT (fraction II) according to the process of the invention with the main components oxidiser 1, esterification column 5, and crude ester rectification 7 and 11. An analysis of the material flows 1.1 to 1.20 defined subsequently and shown in FIG. 1 is indicated in Table I.

In the oxidiser 1, known per se, for example corresponding to DE-C3-28 05 915, a liquid mixture consisting chiefly of p-xylene (material flow 1.1) and p-TE (material flow 1.4) is oxidised with atmospheric oxygen (material flow 1.2) at a temperature of about 160° C. and a pressure of about 7 bar and subject to addition of catalyst (material flow 1.3).

The oxidation product P1 being produced contains as main components p-toluic acid (p-TA) (about 17% by weight), MMT (about 22% by weight), p-toluic acid methylester (p-TE) (about 24% by weight), DMT (about 14% by weight) and terephthalic acid (TA) (about 10% by weight).

Moreover, by-products and impurities, in particular benzoic acid methylester (BME), TAE, HM-BME, high boiling substances etc., are to be found.

In the oxidation, the oxygen contained in the air (material flow 1.2) is consumed up to a residual content. The otherwise remaining nitrogen is saturated with the substances to be found in the oxidiser 1 and leaves as oxidiser discharge gas (material flow 1.5) the oxidiser 1 together with the reaction water being formed in the oxidation, as well as high boiling cracking products like $CO$, $CO_2$, formic acid and acetic acid.

The xylenic mixture denoted as p-xylene (material flow 1.1) consists of freshly employed xylene with an isomer content of 6,000 ppm as well as the xylenic and organic fractions respectively recovered from the material flows 1.5, 1.6 and 1.10.

The para-toluic acid methylester (p-TE) (material flow 1.4) is withdrawn from an intermediate tank which is not shown which is fed predominantly from the head product of the crude ester rectification column 11 (material flow 1.12). In the exemplifying embodiment according to FIG. 1, the organic components of the flows 1.11, 1.16, 1.15 as well as the products recovered from the residue 1.14 are likewise fed into the p-TE intermediate tank.

In the main, the p-TE-flow 1.12 is accordingly fed back into the oxidiser 1 so that a closed circuit exists.

The reaction products being produced in the oxidation have in part high melting points—p-TA of about 180° C., MMT of about 227° C.—or are practically not meltable (terephthalic acid) and are soluble in other substances only to a limited extent so that the danger of a crystallising out and accordingly blockage occurs. As a result of a relatively high amount of p-TE and DMT running in the circuit, this danger can be restricted.

The p-TE-excess employed as well as the DMT quantities running in the circuit serve to increase reaction and adjust melting point of the product flow $P_1$ leaving the oxidiser. Melting points in the region of 140° C. are preferred in this connection.

The acid number, which is held at 200 to 300 g KOH/kg oxidation product at the outlet from the oxidiser, is a valid measure of the well-balanced ratio between high melting acids and other products improving the melting point and flowability. With too high acid numbers, bad flowability and disadvantageous melting points are to be expected and with too low acid numbers, that is too large amounts of circulating products, too high distillation cost in the crude ester distillation columns 7 and 11. The p-TE-excess is so adjusted that the oxidation conditions in the oxidiser remain moderate, that is the temperature lies between 150° and 180° C. at 5 to 8 bar. It has been established that concentrations of 5 to 30% by weight p-TE should be established in the final oxidation product. The quantitative flows shown in Table I are obtained if a small p-TE excess of 24% and an acid number at the outlet from the oxidiser of 225 g KOH/kg oxidation product are maintained.

The oxidation product produced is freed of xylene still contained therein in the stripper 2 by means of steam (material flow 1.7). The vapours which are obtained have a composition 1.6 according to Table I.

The oxidation product flow $P_1$ is next after increasing the pressure by means of the high pressure pump 3, combined with hot methanol (material flow 1.8) and, after heating in the heat exchanger 4 to 250° C., is esterified in the esterification reactor 5 at 250° C. with methanol (material flow 1.9). The methanol is supplied at the sump in the form of vapour. The relatively high methanol excess leaves the head of the column 5 (material flow 1.10) with the reaction water and is saturated with other compounds present at the head of the column 5. The esterified oxidation product, the so-called crude ester, is depressurized to normal pressure in the intermediate tank 6 and is moreover cooled to temperatures of about 200° C. The methanol still present escapes in the form of vapour (material flow 1.11) via a vapour duct and is saturated with the components obtained in the reactor.

Crude Ester Rectification

The crude ester mixture, which still contains by-products like TAE, BME, high boiling substances, HM-BME as well as the catalyst, in addition to DMT (about 58% by weight) and p-TE (about 33% by weight), is pumped into the rectification consisting of two columns 7, 11 from the intermediate container 6.

Figure 2:
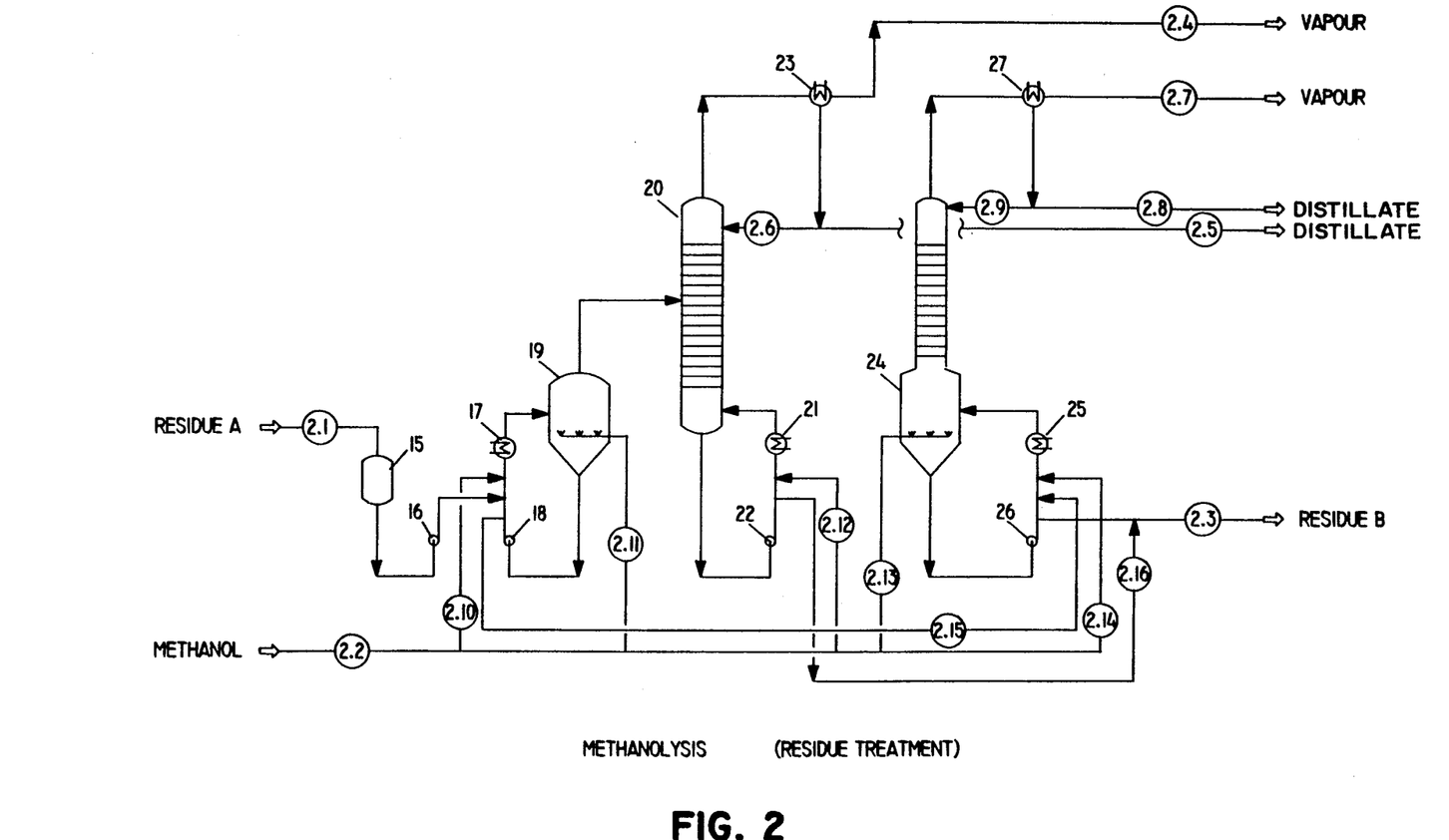

The high boiler column 7 with vaporiser 8 and condenser 9 serves for driving off of high boiling substances contained in the crude ester (material flow 1.14) as sump product, which can be subsequently treated as "Residue A" in a separate residue working up (FIG. 2).

In addition, the "Residue A" contains all of the catalyst as well as a high proportion of about 52% by weight DMT. The largest part of the HM-BME is likewise discharged together with the residue fraction.

As a result of the provided high DMT content in the sump flow 1.14 of the high boiler column 7, the sump temperature can be held at 250° C. and the head pressure at 0.2 bar, with a high temperature level of about 205° C. which makes possible an energetically satisfactory recovery of the condensation heat (condenser 9) in the form of low pressure steam (3.5 bar) being set at the head of the high boiler column 7. The head pressure of about 0.2 bar in the high boiler column 7 is maintained by a vacuum plant which is nor shown, wherein the material flow 1.16 is discharged.

The condensed head product flows from the condenser 9 in the low boiler column 11 with vaporiser 12 and condenser 13 in order to drive off the p-TE fraction. At head temperatures of about 194° C., the condensation heat can be used to produce 3.5 bar low pressure steam. The DMT content in the head product is held high at about 18% by weight so that, inclusive of the amounts of DMT contained in the residue A (material flow 1.14), there is obtained a high circulating amount of DMT and accordingly the acid number of 225 g KOH/kg oxidation product in the oxidate. The relationships set in the exemplifying embodiment shown are obtained from Table I (material flow 1.14 and 1.12). Should relationships which are suitable for the process be set by the choice of the refluxes and amounts, the amounts of TAE and HM-BME in the crude DMT of 0.1% by weight for TAE and 0.05% by weight for HM-BME respectively indicated in Table I are attained.

A sump temperature of 250° C., a head temperature of 194° C. and a head pressure of 0.3 bar are set in the low boiler column 11. The head pressure is maintained by pumping off the flow 1.15 by means of a vacuum plant which is not shown.

The high p-TE quantity obtained at top of column 11 assures a residual content of p-TE in the oxidation product P1 of 24%. The substances HM-BME and TAE important for the quality of crude DMT represent intermediate products of the p-TE oxidation to MMT and can therefore be fed back to the oxidiser with the p-TE distillate and the valuable products obtained from the residue respectively without problem. It is apparent from the reflux ratios or the amounts of vapour in the columns (7,11) that the energy necessary for the distillation is relatively low compared with the process according to DE-C1-30 11 558. In particular it is advantageous that the condensation heat of the low boiler column 11 can be utilised in the form of low pressure steam (3.5 bar).

Recrystallisation

Figure 3:
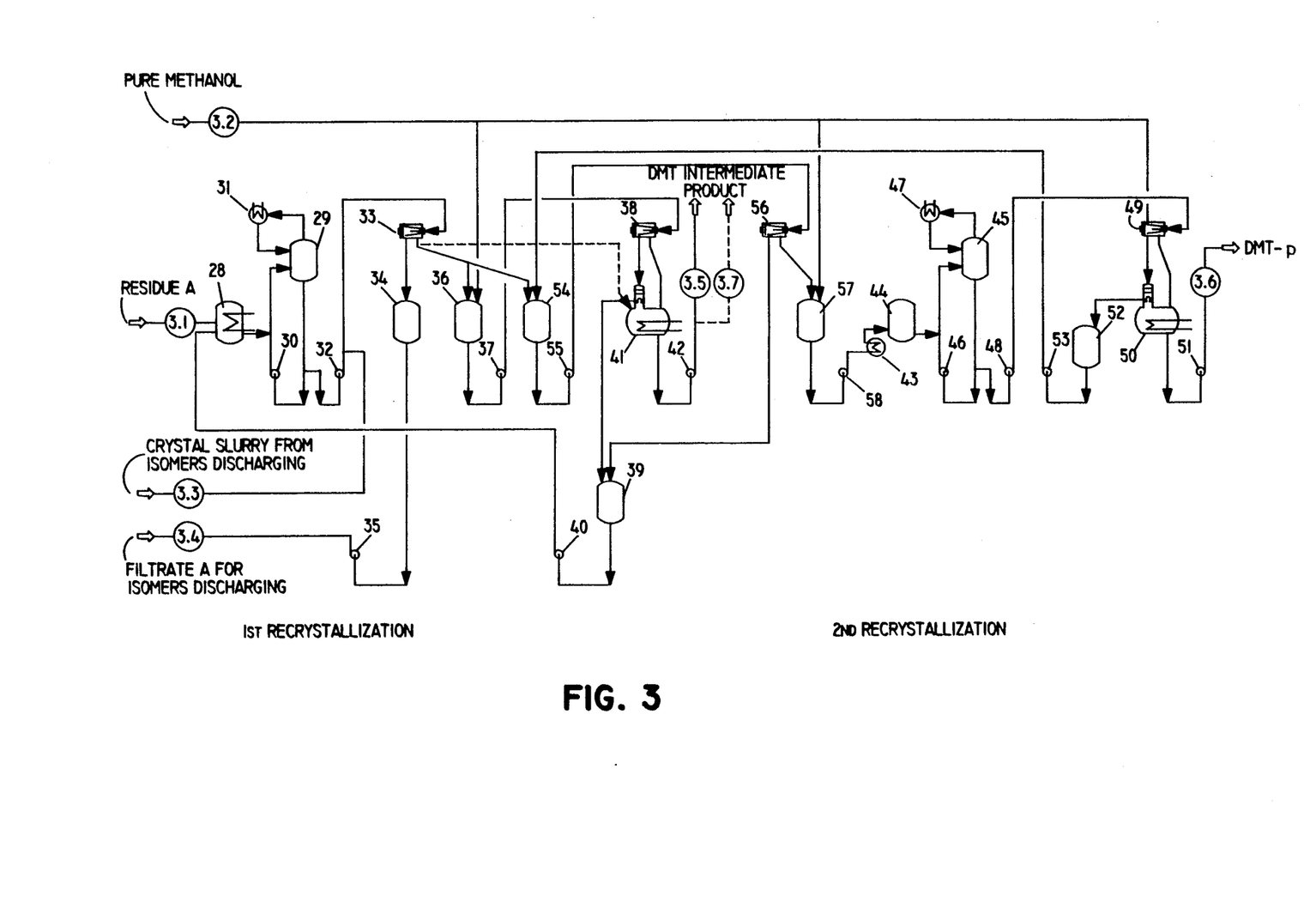
Figure 4:
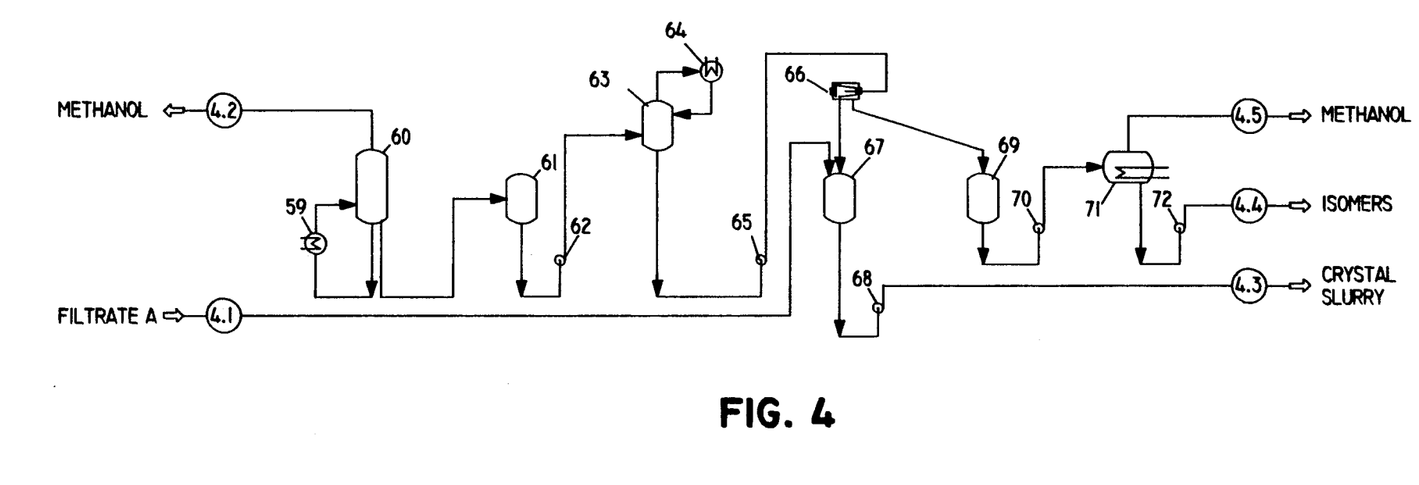

The crude DMT (fraction II) purified according to FIG. 1 by rectification is further purified to the DMT intermediate product by single methanolic solvent recrystallisation (FIG. 3, analyses of the material flows 3.1 to 3.5, see Table III). Moreover the crude DMT (material flow 3.1, correspondingly material flow 1.13 according to FIG. 1) is mixed up in the mixing tank 28 with methanol from the intermediate tank 39. The hot solution is cooled in the crystalliser 29 by means of rotary pump 30 and condenser 31 by release of pressure. The pump 32 conveys the crystalysate to the centrifuge 33 where it is separated into the Filtrate A and the crystalysate. The Filtrate A is fed via tank 34 and pump 35 (material flow 3.4) to the isomer discharge system (FIG. 4)

The separation as completely as possible of the crystallisation product and mother liquor adhering thereto is of decisive significance for the purification effect of the apparently expensive recrystallisation since, with respect to the mother liquor, this is subject to almost all the impurities. A methanolic washing of the crystalysate is therefore carried out in the illustrated exemplifying embodiment to increase the purification effect of the recrystallisation. Moreover, the crystalysate is mixed in the tank 36 with freshly distilled methanol and supplied via a pump 37 to the centrifuge 38. The filtrate being produced—an only slightly impure methanol—is supplied to the head of the melter 41, while the crystalysate is conducted into the melter 41.

In the melter 41, the residual mother liquor is driven off from the crystalysate and the DMT melted. The vaporised methanol is condensed in the head of the melter 41 and fed together with the filtrate from the centrifuge 38 into the intermediate tank 39 for methanol.

The DMT (material flow 3.5) taken from the melter 41 via the pump 42 represents the DMT intermediate product of desired purity. It can as a matter of choice be worked up by hydrolysis (FIGS. 5 and 6) to terephthalic acid or can be worked up by a second recrystallisation to fibregrade DMT (DMT-p), with the combination of these possibilities, in particular offering surprising advantages. The DMT intermediate product (material flow 3.5) still contains only very little impurities of TAE and HM-BME, of a maximum of 100 ppm, in the indicated explanatory example of only 17 ppm (see Table III), as well as small amounts of the isomer DMI and DMO, in the illustrated exemplifying embodiment, together 67 ppm.

Processing of filtrate

The filtrate removed from the intermediate tank 34 (FIG. 3) via the pump 35 (material flow 3.4, FIG.

3=material flow 4.1, FIG. 4) is initially concentrated by evaporation in the vaporiser 59 with separator 60 so that the concentrated mixture consists of up to ⅔ of methanol and ⅓ of dissolved substance (DMT+impurities). The evaporation pressure is 4 bar and the temperature is 100° C. The remaining solution is stored under this pressure in the tank 61 and pumped by means of a pump 62 into the crystalliser 63 with condenser 64, where the solution is cooled by evaporation cooling to about 25° C.

The corresponding suspension is supplied via pump 65 to the centrifuge 66 and separated into a filtrate and the crystalysate. The crystalysate can, as shown in FIG. 4, be fed back via pump 68 to the first recrystallisation as suspension mixed in stirrer tank 67 with methanol (material flow 4.3 in FIG. 4, material flow 3.3 in FIG. 3).

The filtrate is conducted into the collecting tank 69 and from there by means of the pump 70 to the vaporiser 71 in which the methanol is evaporated off completely (material flow 4.5, Table 4). The remaining mixture consists predominantly of DMI (37% by weight) and DMO (26% by weight) and contains only relatively small amounts of valuable products, in particular DMT (16% by weight), TAE (10% by weight) as well as 5% by weight each of p-TA and HM-BME so that they are discharged completely without great losses via the pump 72 (material flow 4.4), in particular to undergo combustion.

Processing of residue

"Residue A" according to FIG. 1 (material flow 1.14, Table I=material flow 2.1, Table II) is stored in tank 15 (FIG. 2). Residue A contains, in addition to DMT (about 52% by weight), predominantly high boiling substances (37% by weight) as well as the catalyst (about 1% by weight).

The acids still present in Residue A are afterwards esterified in the two-step methanolysis according to FIG. 2, a part of the high boiling, in particular binuclear aromatic, compounds are cleaved and the valuable products (DMT, HM-BME, methoxymethylbenzoic acid methylester [MM-BME] and p-TE) are separated from the remaining undesired high boiling substances. The valuable products are fed back into the oxidation while the undesired high boiling substances are discharged from the process.

Among the distillable high boiling substances found in residue A are substances which, insofar as they are fed back into the oxidation, influence yields or selectivity of the oxidation disadvantageously since they influence the effectiveness of the catalyst system. Moreover such substances can, during the oxidative treatment, form cleavage products e.g. $CH_3$-DMT isomers, which are disadvantageous for the quality of the crude DMT, can only be removed distillatively with difficulty from the crude ester and require additional purification expenditure in the subsequent crystallisation if high purity polyester crude substances are to be produced. The feeding back of such high boiling substances into the oxidation must therefore be avoided.

The following reaction guidance is given in the illustrated exemplifying embodiment:

Residue A from the crude ester distillation is run from the tank 15 by means of the pump 16 into a circulating system which consists of pump 18, heat exchanger 17 and reactor 19. At the same time, methanol in the form of vapour (material flow 2.10) is pumped into the circulation. As a result of the presence of the methanol, residual amounts of esterified high boiling acids which are still contained are esterified and to some extent taken up by the high methanol vapour excess and flashed in the form of vapour into the vapour space of the reactor 19. The amount of liquid which is not vaporised remains in the sump part of the reactor 19 and is treated afresh with methanol vapour and cleaved methanolytically again. The esters being produced remain in the methanolic vapour phase and are conducted together with the distillable constituents of the residue and the flash product into the distillation column 20. The temperature in the reactor 19 chosen in the exemplifying embodiment amounts to 265° to 270° C., whereas the temperature in column 20 is at about 250° C., so that a part of the high boiling constituents can be withdrawn at the sump of the column 20. The high boiling by-products are concentrated in the operating part of the distillation column 20, and withdrawn at the sump of the column. A part of the high boiling product is discharged, while the rest, mixed with methanol vapour, is fed back via pump 22 and vaporiser 21 to the sump of the column. Until the distillable high boiling substances, which do not represent valuable products and therefore, as mentioned above, leave the sump of the column 20 as high boiling substances, all valuable products are directed with the methanol vapour to the dephlegmator 23 and condensed. A part of the condensate is used as reflux, whereas the rest is discharged (material flow 2.5) and is mixed with the p-TE flow for the oxidation. The methanol excess (material flow 2.4) is directed together with the water being produced in the methanolysis and post-esterification to a methanol dewatering column (not shown).

A part of the circulating flow from the reactor 19 is discharged from the circuit and subjected to a further methanolysis step in the reactor 24 with heat exchanger 25, circulating pump 26 and dephlegmator 27. This second methanolysis step is carried out at a temperature of >275° C., so that further high molecular compounds of Residue A are split off. The products leaving the reactor 24 in gaseous form are condensed completely in the dephlegmator 27, with the exception of the methanol, while the methanol (material flow 2.7) together with the methanol from the dephlegmator 23 is discharged for reuse in the general process. The products condensed in the dephlegmator 27 are for the largest part fed back together with the p-TE flow into the oxidation, while a small part is fed back as reflux to the head of the column of the reactor 24. The constituents which have not vaporised are withdrawn at the sump of the reactor 24 and discharged partly for catalyst recovery (material flow 2.3) while the remainder is led back by means of pump 26 via vaporiser 25 to the reactor. In addition methanol in the form of vapour is supplied to the reactor circulation.

EXAMPLE 2

The washing of the DMT crystalysate can possibly be dispensed if not especially high requirements are placed on the purity of the DMT intermediate product, e.g. for the production of medium pure terephthalic acid (MTA). In FIG. 3, this alternative for the production of DMT intermediate product is shown in broken line. The DMT intermediate product (product flow 3.7) withdrawn from the melter still contained about 150 ppm of TAE and HM-BME as well as 580 ppm of isomers DMI and DMO.

EXAMPLE 3

The simultaneous production of fibregrade DMT (DMT-p) and DMT-intermediate products for terephthalic acid production is shown to a further extent in FIG. 3. For this purpose, the crystalysate flow from the centrifuge is distributed to mixing tanks 36 and 54. The DMT crystalysate is mixed with methanol from the intermediate tank 52 in the mixing tank 54 and supplied via the pump 55 to the centrifuge 56. The filtrate being produced is supplied to the methanol intermediate tank 39, while the crystalysate in the mixing tank 57 is mixed with pure methanol and is supplied via the pump 58 and heat exchanger 43 to the intermediate tank 44. The DMT dissolved in methanol is further purified in the second recrystallisation consisting of crystallyser 45, heat exchanger 47 and pump 46. The crystal suspension is then supplied, via the pump 48 to the washing centrifuge 49 where it is distributed into a filtrate and a crystalysate flow. The crystalysate is then melted in melter 50 and freed from residual mother liquor while the filtrate is directed via the condensation head of the melter 50 to the intermediate tank 52. The filtrate consisting almost exclusively of methanol is fed back via the pump 53 to the mixing tank 54 (countercurrent). The DMT-p produced is withdrawn by means of the pump 51 to the melter 50. It contains less than 10 ppm of isomers and only about 2 ppm TAE and HM-BME (material flow 3.6) and represents accordingly a fibregrade DMT with—for large scale industrial plants—hitherto unachieved purity.

EXAMPLE 4

Hydrolysis (PTA)

Figure 5:
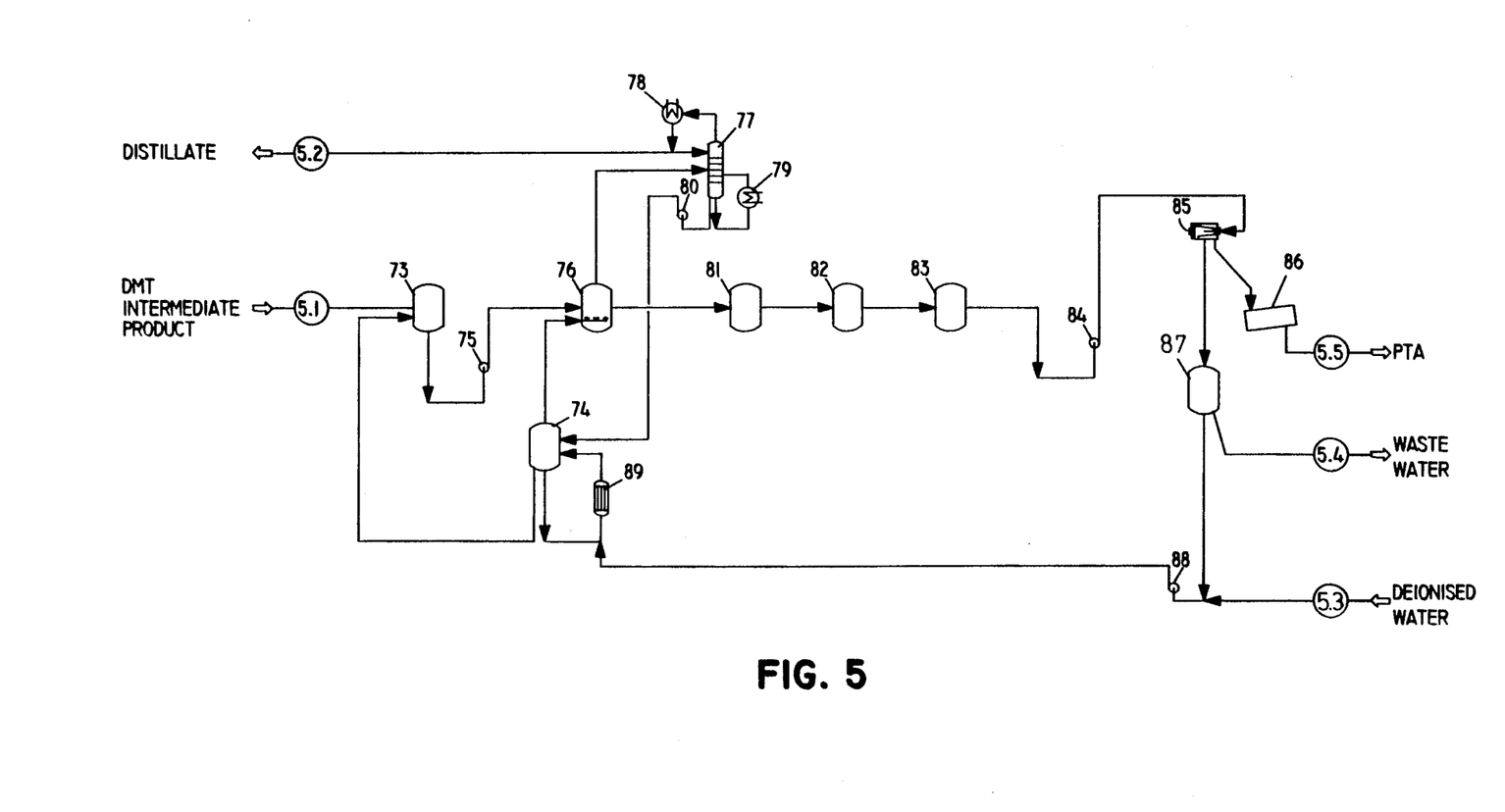

The hydrolysis of the DMT intermediate product according to FIG. 3 (material flow 3.5) to fibre pure terephthalic acid (PTA) is explained more precisely with reference to FIG. 5.

The DMT intermediate product (material flow 5.1) coming from the first recrystallisation (FIG. 3) is mixed in mixing tank 73 with water from the stripping steam producer 74 in the ratio 1:1 and partially hydrolysed. The suspension is pumped into the hydrolysis reactor 76 by means of the pump 75, in which the mixture is treated with stripping steam from the stripping steam producer 74. In this way the methanol being freed in the hydrolysis together with steam and the dimethylether formed is driven off in the hydrolysis column 77 with condenser 78 and heat exchanger 79. By suitable choice of the reflux ratio, the result is attained that a methanol free water can be withdrawn at the sump of the column 77 with the help of the pump 80 and can be fed back into the stripping steam producer. The condensed head product (material flow 5.2) consists chiefly of dimethylether (DME), methanol and water and can be supplied to a methanol rectification (not shown) after distillative separation off of the DME. The dimethylether is burned off while the methanol is fed back into the esterification (FIG. 1). From the reactor 76, the terephthalic acid being produced is crystallised out in a three-step expansion crystallisation (crystallisers 81, 82 and 83) and conveyed to the centrifuge 85 by means of pump 84. The crystal slurry is supplied to the drier 86 and dried there to form pure terephthalic acid (PTA) (material flow 5.5). The mother liquor running out from the centrifuge 85 into the collecting tank 87 is discharged, partially as waste water (material flow 5.4) for removal of still dissolved isomers (ITA, OTA) and of foreign substances which arise for example by wear of the mechanically moved parts like slide ring seals etc. The largest part of the filtrate is however fed back by means of the pump 88 to the stripping vapour producer with heat exchanger 89. The water used in the hydrolysis and withdrawn in the distillate (material flow 5.2) as well as in the waste water (material flow 5.4) is replaced by fresh deionised water (material flow 5.3).

The temperature in the mixing tank 73 and in the hydrolysis reactor 76 amounts in the illustrated exemplifying embodiment to about 265° C. The expansion crystallisation was conducted at up to a temperature of 95° C. As is to be seen from Table V (material flow 5.5) the PTA has in addition to about 100 ppm MMT still only about 40 ppm of further impurities and is accordingly suitable for almost all usages.

EXAMPLE 5

Hydrolysis (PTA-p)

Figure 6:
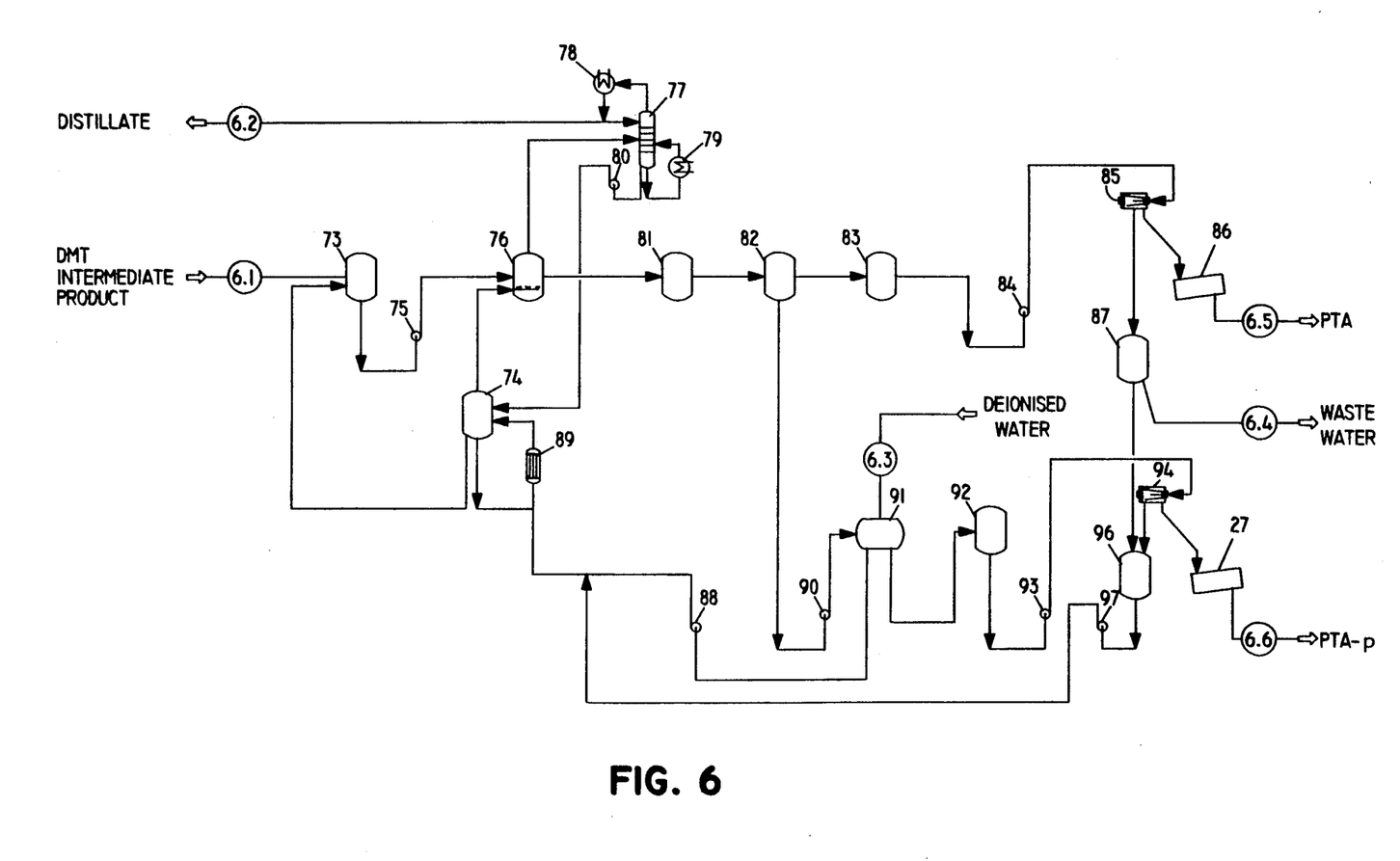

Should a terephthalic acid with hitherto unachieved low content of MMT and p-TA (PTA-p) be desired, the PTA in the connection to the crystallisation can optionally be washed once again with deionised water. The combined production of PTA and PTA-p according to FIG. 6 is especially advantageous. The arrangements 73 to 89 and the procedure correspond moreover largely to FIG. 5. Only in the crystallyser 82 is a part of the crystal slurry withdrawn by means of pump 90 and pumped into the countercurrent washer 91, e.g. according to DE-A-11 -b 36 39 958, where it is washed in countercurrent with deionised water (material flow 6.3). The washing takes place at a temperature of 190° C. The washed crystal suspension is released into the crystalliser 92 and conveyed from there by means of the pump 93 to the centrifuge 94 for separating off of the mother liquor. The damp PTA is dried in the drier 95 and leaves the plant as high purity PTA-p with a total content of impurities inclusive of MMT and p-TA of <50 ppm (material flow 6.6, Table 6) while the mother liquor running off from the centrifuge 94 is combined in the tank 96 with the mother liquor running off from the centrifuge 85 and is pumped by means of pump 97 into the stripping stream producer 74.

Pump 88 conveys the mother liquor from the countercurrent washing 91 back into the stripping stream producer 74.

Abbreviations

DME—Dimethylether
DMI—Dimethyl isophthalate
DMO—Dimethyl orthophthalate
DMT—Dimethyl terephthalate
DMT-p—Pure DMT (fibregrade DMT)
HM-BME—Hydroxymethylbenzoic acid methyl ester
ITA—Isophthalic acid
MM-BME—Methoxymethylbenzoic acid methyl ester
MMT—Monomethyl terephthalate
MTA—Medium pure terephthalic acid
OTA—Orthophthalic acid
p-TA—para-Toluic acid
p-TE—para-Toluic acid methyl ester (pT-ester)
p-X—para-Xylene
PTA—Pure terephthalic acid (fibregrade TA)
PTA-p—Terephthalic acid of very high purity (content of MMT and p-TA <50 ppm)
TA—Terephthalic acid
TAE—Terephthalaldehydic acid methyl ester TAS—Terephthalaldehydic acid (4-CBA)

Definitions

In the description, % and ppm amounts used relate, unless otherwise indicated, to parts by weight

| Legend | | |
|---|---|---|
| 1 - | Oxidiser | |
| 2 - | Stripper | |
| 3 - | High pressure pump | |
| 4 - | Heat Exchanger | |
| 5 - | Esterification column | |
| 6 - | Intermediate tank | |
| 7 - | Crude ester rectification (high boiler column) | |
| 8 - | Evaporator | |
| 9 - | Condenser | |
| 10 - | Pump | |
| 11 - | Crude ester rectification (low boiler column) | |
| 12 - | Vaporiser | |
| 13 - | Condenser | |
| 14 - | Pump | |
| 15 - | Tank | |
| 16 - | Pump | |
| 17 - | Heat Exchanger | |
| 18 - | Pump | |
| 19 - | Reactor | |
| 20 - | Distillation column | |
| 21 - | Vaporiser | |
| 22 - | Pump | |
| 23 - | Dephlegmator | |
| 24 - | Reactor | |
| 25 - | Heat Exchanger | |
| 26 - | Circulating pump | |
| 27 - | Dephlegmator | |
| 28 - | Mixing Tank | |
| 29 - | Crystallizer | |
| 30 - | Circulating Pump | |
| 31 - | Condenser | |
| 32 - | Pump | |
| 33 - | Centrifuge | |
| 34 - | Tank | |
| 35 - | Pump | |
| 36 - | Tank | |
| 37 - | Pump | |
| 38 - | Centrifuge | |
| 39 - | Methanol-intermediate tank | |
| 40 - | Pump | |
| 41 - | Melter | |
| 42 - | Pump | |
| 43 - | Heat exchanger | |
| 44 - | Intermediate tank | |
| 45 - | Crystalliser | |
| 46 - | Pump | |
| 47 - | Heat Exchanger | |
| 48 - | Pump | |
| 49 - | Washing centrifuge | |
| 50 - | Melter | |
| 51 - | Pump | |
| 52 - | Intermediate tank | |
| 53 - | Pump | |
| 54 - | Mixing tank | |
| 55 - | Pump | |
| 56 - | Centrifuge | |
| 57 - | Mixing tank | |
| 58 - | Pump | |
| 59 - | Evaporator | |
| 60 - | Separator | |
| 61 - | Tank | |
| 62 - | Pump | |
| 63 - | Crystalliser | |
| 64 - | Condenser | |
| 65 - | Pump | |
| 66 - | Centrifuge | |
| 67 - | Stirring Tank | |
| 68 - | Pump | |
| 69 - | Collecting Tank | |
| 70 - | Pump | |
| 71 - | Evaporator | |
| 72 - | Pump | |
| 73 - | Mixing Tank | |
| 74 - | Stripping Vapour producer | |
| 75 - | Pump | |
| 76 - | Hydrolysis reactor | |
| 77 - | Hydrolysis column | |
| 78 - | Condenser | |
| 79 - | Heat Exchanger | |
| 80 - | Pump | |
| 81 - | Crystalliser | |
| 82 - | Crystalliser | |
| 83 - | Crystalliser | |
| 84 - | Pump | |
| 85 - | Centrifuge | |
| 86 - | Drier | |
| 87 - | Collecting Tank | |
| 88 - | Pump | |
| 89 - | Heat Exchanger | |
| 90 - | Pump | |
| 91 - | Countercurrent washer | |
| 92 - | Crystalliser | |
| 93 - | Pump | |
| 94 - | Centrifuge | |
| 95 - | Drier | |
| 96 - | Tank | |
| 97 - | Pump | |

TABLE I

| | Stream No. | | | | | | | | | |
|---|---|---|---|---|---|---|---|---|---|---|
| | 1.1 Xylene to oxid. (after separation) | | 1.2 Process air to oxidation | | 1.3 Catalyst to oxidation | | 1.4 p-TE to oxidation | | 1.5 Discharge gas from oxidation | |
| Components | kg/h | wt % | kg/h | wt % | kg/h | wt % | kg/h | wt % | kg/h | wt % |
| High boilers | — | — | | | | | — | — | | |
| DMT + DMI + DMO | 191,8 | 0,58 | | | | | 11244,6 | 22,48 | 118,7 | 0,12 |
| MM-BME | | | | | | | 379,2 | 0,76 | | |
| MMT | | | | | | | 516,1 | 1,03 | | |
| HM-BME | | | | | | | 499,1 | 0,99 | | |
| TA | | | | | | | — | — | | |
| TAE | 15,8 | 0,05 | | | | | 1144,2 | 2,29 | 15,8 | 0,02 |
| p-TE | 5189,0 | 15,63 | | | | | 32473,3 | 64,92 | 2137,1 | 2,21 |
| TAS | — | — | | | | | — | — | | |
| p-TA | 102,9 | 0,31 | | | | | — | — | 102,9 | 0,11 |
| BME | 2239,5 | 6,75 | | | | | 3556,6 | 7,11 | 1266,4 | 1,31 |
| Benzoic acid | — | — | | | | | | | — | — |
| p-X | 25318,5 | 76,28 | | | | | | | 5960,1 | 6,17 |
| Acetic acid | | | | | | | | | 441,8 | 0,46 |
| Cobalt | | | | | 32,08 | 6,91 | | | — | — |
| Manganese | | | | | 7,76 | 1,68 | | | | |
| Formic acid | | | | | | | | | 220,9 | 0,23 |
| Carbon dioxide | | | | | | | | | 1850,8 | 1,92 |
| Methanol | | | | | | | 136,9 | 0,27 | 474,9 | 0,49 |

TABLE I-continued

| Components | | | | | | | | | |
|---|---|---|---|---|---|---|---|---|---|
| Oxygen | | | 21720,4 | 22,86 | | | | 2732,3 | 2,83 |
| Nitrogen | | | 71902,1 | 75,69 | | | | 71902,1 | 74,51 |
| Carbon monoxide | | | — | — | | | | 462,7 | 0,48 |
| Water | 133,5 | 0,40 | 1377,5 | 1,45 | 424,16 | 91,41 | 69,0 | 0,15 | 7915,2 | 8,20 |
| Light ends | — | — | — | — | — | — | — | — | 900,3 | 0,94 |
| Σ Total | 33191 | 100,00 | 95000 | 100,00 | 464 | 100,00 | 50019 | 100,00 | 96502 | 100,00 |

| | Stream No. | | | | | |
|---|---|---|---|---|---|---|
| | 1.6 Vapour from stripper | | 1.7 Steam to stripper | | P₁ Oxidation product upstream stripper | |
| Components | kg/h | wt % | kg/h | wt % | kg/h | wt % |
| High boilers | | | | | 2062,5 | 2,51 |
| DMT + DMI + DMO | | | | | 11101,4 | 13,51 |
| MM-BME | | | | | — | — |
| MMT | | | | | 18466,4 | 22,47 |
| HM-BME | | | | | 164,3 | 0,20 |
| TA | | | | | 8307,6 | 10,11 |
| TAE | | | | | 394,4 | 0,48 |
| p-TE | 616,2 | 9,34 | | | 19722,3 | 24,00 |
| TAS | | | | | 714,9 | 0,87 |
| p-TA | | | | | 14330,8 | 17,44 |
| BME | 308,1 | 4,67 | | | 4839,9 | 5,89 |
| Benzoic acid | — | — | | | 82,2 | 0,10 |
| p-X | 1232,4 | 18,68 | | | 1232,6 | 1,5 |
| Acetic acid | 164,3 | 2,49 | | | 164,3 | 0,20 |
| Cobalt | — | — | | | 10,7 | 0,013 |
| Manganese | — | — | | | 2,5 | 0,003 |
| Formic acid | 82,2 | 1,25 | | | 82,2 | 0,10 |
| Carbon dioxide | | | | | | |
| Methanol | | | | | | |
| Oxygen | | | | | | |
| Nitrogen | | | | | | |
| Carbon monoxide | | | | | | |
| Water | 4193,8 | 63,57 | 3921 | 100,00 | 493,0 | 0,6 |
| Light ends | — | — | | | — | — |
| Σ Total | 6597 | 100,00 | 3921 | 100,00 | 82172 | 100,00 |

| | Stream No. | | | | | | | |
|---|---|---|---|---|---|---|---|---|
| | 1.8 Methanol to oxidate heater | | 1.9 Methanol vapour to esterification | | 1.10 Vapour from esterification | | 1.11 Vapour from crude ester flash | |
| Components | kg/h | wt % | kg/h | wt % | kg/h | wt % | kg/h | wt % |
| High boilers | | | | | — | — | — | — |
| DMT + DMI + DMO | | | | | 73,1 | 0,26 | 1602,3 | 7,50 |
| MM-BME | | | | | — | — | — | — |
| MMT | | | | | | | 516,1 | 2,42 |
| HM-BME | | | | | | | 98,0 | 0,46 |
| TA | | | | | — | — | — | — |
| TAE | | | | | | | 47,6 | 0,22 |
| p-TE | | | | | 2435,7 | 8,81 | 10853,7 | 50,83 |
| TAS | | | | | — | — | — | — |
| p-TA | | | | | — | — | — | — |
| BME | | | | | 665,0 | 2,41 | 1539,4 | 7,21 |
| Benzoic acid | | | | | | | | |
| p-X | | | | | | | | |
| Acetic acid | | | | | | | | |
| Cobalt | | | | | | | | |
| Manganese | | | | | | | | |
| Formic acid | | | | | | | | |
| Carbon dioxide | | | | | | | | |
| Methanol | 3613,0 | 100,00 | 32154,0 | 100,00 | 18562,9 | 67,15 | 6501,4 | 30,45 |
| Oxygen | | | | | | | | |
| Nitrogen | | | | | | | | |
| Carbon monoxide | | | | | | | | |
| Water | | | | | 5825,6 | 21,07 | 194,5 | 0,91 |
| Light ends | | | | | 82,7 | 0,30 | — | — |
| Σ Total | 3613,0 | 100,00 | 32154,0 | 100,00 | 27645 | 100,00 | 21353 | 100,00 |

| | Stream No. | | | | | | | | |
|---|---|---|---|---|---|---|---|---|---|
| | 1.12 p-TE distillate from crude DMT still | | 1.13 crude DMT to recrystallisation | | 1.14 Residue A | | 1.15 Vacuum gas from crude DMT still | | 1.16 Vacuum gas from crude ester still | |
| Components | kg/h | wt % | kg/h | wt % | kg/h | wt % | kg/h | wt % | kg/h | wt % |
| High boilers | — | — | — | — | 2261,6 | 36,83 | — | — | — | — |
| DMT + DMI + DMO | 4789,8 | 18,16 | 29641,7 | 99,80 | 3167,0 | 51,57 | 47,5 | 2,19 | 265,9 | 13,13 |
| MM-BME | — | — | — | — | — | — | | | | |
| MMT | — | — | — | — | 610,7 | 9,94 | | | | |
| HM-BME | — | — | 14,8 | 0,05 | 51,5 | 0,84 | | | | |
| TA | — | — | — | — | | | | | | |
| TAE | 1053,2 | 4,00 | 29,7 | 0,10 | | | 26,5 | 1,22 | 16,9 | 0,83 |

TABLE I-continued

| Components | | | | | | | | | |
|---|---|---|---|---|---|---|---|---|---|
| p-TE | 18788,8 | 71,34 | — | — | | | 1643,6 | 75,59 | 1107,7 | 54,71 |
| TAS | — | — | — | — | | | — | — | — | — |
| p-TA | — | — | 14,8 | 0,05 | | | — | — | — | — |
| BME | 1704,2 | 6,47 | | | | | 352,4 | 16,21 | 262,0 | 12,94 |
| Benzoic acid | | | | | | | | | | |
| p-X | | | | | | | | | | |
| Acetic acid | | | | | | | | | | |
| Cobalt | | | | | 40,4 | 0,66 | | | | |
| Manganese | | | | | 9,8 | 0,16 | | | | |
| Formic acid | | | | | | | | | | |
| Carbon dioxide | | | | | | | | | | |
| Methanol | | | | | | | 41,1 | 1,89 | 290,2 | 14,33 |
| Oxygen | | | | | | | — | — | — | — |
| Nitrogen | | | | | | | 56,0 | 2,58 | 56,0 | 2,77 |
| Carbon monoxide | | | | | | | — | — | — | — |
| Water | | | | | | | 6,9 | 0,32 | 26,3 | 1,29 |
| Light ends | | | | | | | — | — | — | — |
| Σ Total | 26366,0 | 100,00 | 29701,0 | 100,00 | 6141,0 | 100,00 | 2174,0 | 100,00 | 2025,0 | 100,00 |

| | Stream No. | | | | | | | |
|---|---|---|---|---|---|---|---|---|
| | 1.17 Feed to crude ester still | | 1.18 Reflux to crude ester still | | 1.19 Distillate of crude ester still | | 1.20 Reflux to crude DMT still | |
| Components | kg/h | wt % | kg/h | wt % | kg/h | wt % | kg/h | wt % |
| High boilers | 2261,6 | 3,41 | — | — | — | — | — | — |
| DMT + DMI + DMO | 37911,9 | 57,21 | 17079,1 | 59,29 | 34479,0 | 59,29 | 7350,03 | 18,19 |
| MM-BME | — | — | — | — | — | — | — | — |
| MMT | 610,7 | 0,92 | — | — | — | — | — | — |
| HM-BME | 66,3 | 0,10 | 7,3 | 0,03 | 14,8 | 0,03 | — | — |
| TA | — | — | — | — | — | — | — | — |
| TAE | 1126,3 | 1,70 | 549,5 | 1,91 | 1109,4 | 1,91 | 1616,28 | 4,00 |
| p-TE | 21540,1 | 32,51 | 10121,2 | 35,13 | 20432,4 | 35,13 | 28826,35 | 71,34 |
| TAS | — | — | — | — | — | — | — | — |
| p-TA | 14,8 | 0,02 | 7,3 | 0,03 | 14,8 | 0,03 | — | — |
| BME | 2318,6 | 3,50 | 1018,8 | 3,53 | 2056,6 | 3,53 | 2614,34 | 6,47 |
| Benzoic acid | — | — | | | | | | |
| p-X | — | — | | | | | | |
| Acetic acid | — | — | | | | | | |
| Cobalt | 40,4 | 0,06 | | | | | | |
| Manganese | 9,8 | 0,02 | | | | | | |
| Formic acid | — | — | | | | | | |
| Carbon dioxide | — | — | | | | | | |
| Methanol | 331,5 | 0,50 | 20,4 | 0,07 | 9.841,4 | 0,07 | | |
| Oxygen | — | — | — | — | — | — | | |
| Nitrogen | — | — | — | — | — | — | | |
| Carbon monoxide | — | — | — | — | — | — | | |
| Water | 33,2 | 0,05 | 3,4 | 0,01 | 6,9 | 0,01 | | |
| Light ends | — | — | — | — | — | — | | |
| Σ Total | 66265,0 | 100,00 | 28807,0 | 100,00 | 58155,0 | 100,00 | 40407,0 | 100,00 |

TABLE II

| | Stream No. | | | | | | | | | |
|---|---|---|---|---|---|---|---|---|---|---|
| | 2.1 Residue A from crude ester still | | 2.2 Methanol from filtrate evaporation | | 2.3 Residue B to catalyst recovery | | 2.4 Vapour from re-esterification column | | 2.5 Distillate from re-esterification column | |
| Components | kg/h | wt % | kg/h | wt % | kg/h | wt % | kg/h | wt % | kg/h | wt % |
| High boilers | 2261,6 | 36,83 | | | 876,1 | 91,73 | — | — | — | — |
| DMT + DMI + DMO | 3167,0 | 51,57 | | | 28,7 | 3,01 | 436,6 | 6,04 | 3063,0 | 96,93 |
| MM-BME | — | — | | | — | — | — | — | — | — |
| MMT | 610,7 | 9,94 | | | | | — | — | — | — |
| HM-BME | 51,5 | 0,84 | | | | | 2,7 | 0,04 | 44,5 | 1,21 |
| TA | | | | | | | — | — | — | — |
| TAE | | | | | | | — | — | — | — |
| p-TE | | | | | | | 1,7 | 0,02 | 1,7 | 0,05 |
| TAS | | | | | | | | | | |
| p-TA | | | | | | | | | | |
| BME | | | | | | | | | | |
| Benzoic acid | | | | | | | | | | |
| p-X | | | | | | | | | | |
| Acetic acid | | | | | | | | | | |
| Cobalt | 40,4 | 0,66 | | | 40,4 | 4,23 | | | | |
| Manganese | 9,8 | 0,16 | | | 9,8 | 1,03 | | | | |
| Formic acid | | | | | | | | | | |
| Carbon dioxide | | | | | | | | | | |
| Methanol | | | 13238,0 | 100,00 | | | 6766,6 | 93,55 | 50,3 | 1,59 |
| Oxygen | | | | | | | — | — | — | — |
| Nitrogen | | | | | | | — | — | — | — |
| Carbon monoxide | | | | | | | — | — | — | — |
| Water | | | | | | | 25,4 | 0,35 | 0,5 | 0,02 |

TABLE II-continued

| | | | | | | | | | |
|---|---|---|---|---|---|---|---|---|---|
| Light ends | | | | | — | | — | | — | — |
| Σ Total | 6141,0 | 100,00 | 13238,0 | 100,00 | 955,0 | 100,00 | 7233,0 | 100,00 | 3160,0 | 100,00 |

| | Stream No. | | | | | | | | | |
|---|---|---|---|---|---|---|---|---|---|---|
| | 2.6 Reflux to re-esterification column | | 2.7 Vapour from reactor column | | 2.8 Distillate from reactor column | | 2.9 Reflux to reactor column | | 2.15 Residue from re-esterification reactor | |
| Components | kg/h | wt % | kg/h | wt % | kg/h | wt % | kg/h | wt % | kg/h | wt % |
| High boilers | — | — | — | — | — | — | — | — | 1966,9 | 78,58 |
| DMT + DMI + DMO | 2322,5 | 96,93 | 204,3 | 3,15 | 834,6 | 53,95 | 1733,4 | 53,95 | 474,6 | 18,96 |
| MM-BME | — | — | 34,0 | 0,52 | 345,1 | 22,31 | 716,8 | 22,31 | — | — |
| MMT | — | — | — | — | — | — | — | — | | |
| HM-BME | 33,7 | 1,41 | 38,6 | 0,60 | 313,6 | 20,27 | 651,3 | 20,27 | 7,4 | 0,30 |
| TA | — | — | — | — | — | — | — | — | | |
| TAE | — | — | — | — | — | — | — | — | | |
| p-TE | 1,3 | 0,05 | 50,1 | 0,77 | 26,2 | 1,69 | 54,3 | 1,69 | | |
| TAS | | | | | | | | | | |
| p-TA | | | | | | | | | | |
| BME | | | | | | | | | | |
| Benzoic acid | | | | | | | | | | |
| p-X | | | | | | | | | | |
| Acetic acid | | | | | | | | | | |
| Cobalt | | | | | | | | | 40,4 | 1,61 |
| Manganese | | | | | | | | | 9,8 | 0,39 |
| Formic acid | | | | | | | | | — | — |
| Carbon dioxide | | | | | | | | | — | — |
| Methanol | 38,1 | 1,59 | 6142,0 | 94,73 | 27,5 | 1,78 | 57,2 | 1,78 | 3,9 | 0,16 |
| Oxygen | — | — | — | — | | | | | | |
| Nitrogen | — | — | — | — | | | | | | |
| Carbon monoxide | — | — | — | — | | | | | | |
| Water | 0,4 | 0,02 | 15,0 | 0,23 | | | | | | |
| Light ends | — | — | — | — | | | | | | |
| Σ Total | 2396,0 | 100,00 | 6484,0 | 100,00 | 1547,0 | 100,00 | 3213,0 | 100,00 | 2503,0 | 100,00 |

| | Stream No. | | | | | | | | | |
|---|---|---|---|---|---|---|---|---|---|---|
| | 2.16 Sump product of re-esterification column | | | | 2.10 | 2.11 | 2.12 | 2.13 | 2.14 | |
| Components | kg/h | wt % | kg/h | wt % | kg/h | kg/h | kg/h | kg/h | kg/h | |
| High boilers | 142,5 | 95,00 | | | 1530 | 4580 | 795 | 4743 | 1590 | |
| DMT + DMI + DMO | 7,5 | 5,00 | | | Methanol vapour see stream no. 2.2 | | | | | |
| MM-BME | | | | | | | | | | |
| MMT | | | | | | | | | | |
| HM-BME | | | | | | | | | | |
| TA | | | | | | | | | | |
| TAE | | | | | | | | | | |
| p-TE | | | | | | | | | | |
| TAS | | | | | | | | | | |
| p-TA | | | | | | | | | | |
| BME | | | | | | | | | | |
| Benzoic acid | | | | | | | | | | |
| p-X | | | | | | | | | | |
| Acetic acid | | | | | | | | | | |
| Cobalt | | | | | | | | | | |
| Manganese | | | | | | | | | | |
| Formic acid | | | | | | | | | | |
| Carbon dioxide | | | | | | | | | | |
| Methanol | | | | | | | | | | |
| Oxygen | | | | | | | | | | |
| Nitrogen | | | | | | | | | | |
| Carbon monoxide | | | | | | | | | | |
| Water | | | | | | | | | | |
| Light ends | | | | | | | | | | |
| Σ Total | 150,0 | 100,00 | | | | | | | | |

TABLE III

| | Stream No. | | | | | | | | | |
|---|---|---|---|---|---|---|---|---|---|---|
| | 3.1 crude DMT for 1st recrystallisation | | 3.2 Pure methanol for recrystallisation | | 3.3 Crystal slurry from isomers discharging | | 3.4 Filtrate A to isomers discharging | | | |
| Components | kg/h | wt % | kg/h | wt % | kg/h | wt % | kg/h | wt % | kg/h | wt % |
| DMT | 29463,4 | 99,2 | | | 1172,9 | 35,16 | 1219,4 | 2,05 | | |
| DMI | 104,0 | 0,35 | | | 21,95 | 0,66 | 125,07 | 0,21 | | |
| DMO | 74,3 | 0,25 | | | 15,55 | 0,47 | 89,22 | 0,15 | | |
| HM-BME | 14,8 | 0,05 | | | 3,15 | 0,09 | 17,78 | 0,03 | | |
| TAE | 29,7 | 0,10 | | | 6,30 | 0,19 | 35,75 | 0,06 | | |
| p-TA | 14,8 | 0,05 | | | 3,15 | 0,09 | 17,78 | 0,03 | | |
| Methanol | — | — | 55873 | 100,00 | 2113,0 | 63,34 | 57986,0 | 97,47 | | |

TABLE III-continued

| | | | | | | | | | |
|---|---|---|---|---|---|---|---|---|---|
| Σ Total | 29701,0 | 100,00 | 55873 | 100,00 | 3336,0 | 100,00 | 59491,0 | 100,00 | |

| | Stream No. | | | | | | | | |
|---|---|---|---|---|---|---|---|---|---|
| | 3.5 Intermediate product for hydrolysis | | 3.6 DMT-p from melter | | 3.7 Intermediate product for hydrolysis | | | | |
| Components | kg/h | wt % | kg/h | wt % | kg/h | wt % | kg/h | wt % | kg/h wt % |
| DMT | 21917,0 | 99,991 | 7499,9 | 99,999 | 21902,14 | 99,92 | | | |
| DMI | 0,85 | 39 ppm | 0,03 | 4,3 ppm | 7,38 | 337 ppm | | | |
| DMO | 0,61 | 28 ppm | 0,02 | 3,1 ppm | 5,27 | 240 ppm | | | |
| HM-BME | 0,15 | 6 ppm | traces | 0,7 ppm | 1,05 | 48 ppm | | | |
| TAE | 0,24 | 11 ppm | traces | 1,2 ppm | 2,11 | 96 ppm | | | |
| p-TA | 0,15 | 6 ppm | traces | 0,7 ppm | 1,05 | 48 ppm | | | |
| Methanol | — | — | — | — | — | Only for MTA production | | | |
| Σ Total | 21919,0 | 100,00 | 7500,0 | 100,00 | | | | | |

TABLE IV

| | Stream No. | | | | | | | | |
|---|---|---|---|---|---|---|---|---|---|
| | 4.1 Filtrate A from 1st recrystallisation | | 4.2 Methanol vapour from filtrate A evaporation | | 4.3 Crystal slurry to 1st recrystallisation | | 4.4 Isomers to burning | | 4.5 Methanol vapour from isomer evaporation | |
| Components | kg/h | wt % | kg/h | wt % | kg/h | wt % | kg/h | wt % | kg/h | wt % |
| DMT | 1219,4 | 2,05 | | | 1172,9 | 35,16 | 46,5 | 16,49 | | |
| DMI | 125,07 | 0,21 | | | 21,95 | 0,66 | 103,12 | 36,57 | | |
| DMO | 89,22 | 0,15 | | | 15,55 | 0,47 | 73,67 | 26,12 | | |
| HM-BME | 17,78 | 0,03 | | | 3,15 | 0,09 | 14,63 | 5,19 | | |
| TAE | 35,75 | 0,06 | | | 6,30 | 0,19 | 29,45 | 10,44 | | |
| p-TA | 17,78 | 0,03 | | | 3,15 | 0,09 | 14,63 | 5,19 | | |
| Methanol | 57986,0 | 97,47 | 54387,0 | 100,00 | 2113,0 | 63,34 | — | — | 1486,0 | 100,00 |
| Σ Total | 59491,0 | 100,00 | 54387,0 | 100,00 | 3336,0 | 100,00 | 282,0 | 100,00 | 1486,0 | 100,00 |

TABLE V

| | Stream No. | | | | | | | | |
|---|---|---|---|---|---|---|---|---|---|
| | 5.1 DMT intermediate product to hydrolysis | | 5.2 Distillate from hydro-methanol distillation | | 5.3 Deionised water | | 5.4 Waste water | | 5.5 PTA | |
| Components | kg/h | wt % | kg/h | wt % | kg/h | wt % | kg/h | wt % | kg/h | wt % |
| DMT | 21917,0 | 99,991 | | | | | | | | |
| DMI | 0,85 | 39 ppm | | | | | | | | |
| DMO | 0,61 | 28 ppm | | | | | | | | |
| HM-BME | 0,15 | 6 ppm | | | | | | | | |
| TAE | 0,24 | 11 ppm | | | | | | | | |
| p-TA | 0,15 | 6 ppm | | | | | 0,1 | 15 ppm | 0,05 | <3 ppm |
| Methanol | | | 6927,0 | 51,84 | | | — | — | — | — |
| ITA | | | | | | | 0,53 | 78 ppm | 0,21 | 11 ppm |
| OTA | | | | | | | 0,37 | 54 ppm | 0,12 | 6 ppm |
| TA | | | | | | | 1,8 | 264 ppm | 18747,44 | 99,98 |
| TAS | | | | | | | — | — | 0,3 | 16 ppm |
| Water | | | 5995,0 | 44,87 | 17000,0 | 100,00 | 6799,30 | 99,87 | — | — |
| DME | | | 439,0 | 3,29 | — | — | — | — | — | — |
| MMT | | | — | — | — | — | 5,9 | 867 ppm | 1,88 | 100 ppm |
| Σ Total | 21919,0 | 100,00 | 13361,0 | 100,00 | 17000,0 | 100,00 | 6808,0 | 100,00 | 18750,0 | 100,00 |

TABLE VI

| | Stream No. | | | | | | | | |
|---|---|---|---|---|---|---|---|---|---|
| | 6.1 DMT intermediate product to hydrolysis | | 6.2 Distillate from hydro-methanol distillation | | 6.3 Deionised water | | 6.4 Waste water | | 6.5 PTA | |
| Components | kg/h | wt % | kg/h | wt % | kg/h | wt % | kg/h | wt % | kg/h | wt % |
| DMT | 21917,0 | 99,991 | | | | | | | | |
| DMI | 0,85 | 39 ppm | | | | | | | | |
| DMO | 0,61 | 28 ppm | | | | | | | | |
| HM-BME | 0,15 | 6 ppm | | | | | | | | |
| TAE | 0,24 | 11 ppm | | | | | | | | |
| p-TA | 0,15 | 6 ppm | | | | | 0,128 | 18 ppm | 0,03 | 2 ppm |
| Methanol | | | 6927,0 | 51,84 | | | — | — | — | — |
| ITA | | | | | | | 0,59 | 87 ppm | 0,14 | 10 ppm |
| OTA | | | | | | | 0,38 | 46 ppm | 0,07 | 5 ppm |
| TA | | | | | | | 1,8 | 264 ppm | 14048,14 | 99,98 |
| TAS | | | | | | | — | — | 0,22 | 16 ppm |
| Water | | | 5995,0 | 44,87 | 17000,0 | 100,00 | 6799,21 | 99,87 | — | — |

TABLE VI-continued

| Components | kg/h | wt % | kg/h | wt % | kg/h | wt % | kg/h | wt % | kg/h | wt % |
|---|---|---|---|---|---|---|---|---|---|---|
| DME | — | — | 439,0 | 3,29 | — | — | — | — | — | — |
| MMT | — | — | — | — | — | — | 5,9 | 867 ppm | 1,4 | 100 ppm |
| Σ Total | 21919,0 | 100,00 | 13361,0 | 100,00 | 17000,0 | 100,00 | 6808,0 | 100,00 | 14050,0 | 100,00 |

| | Stream No. 6.6 PTA-p | |
|---|---|---|
| Components | kg/h | wt % |
| DMT | | |
| DMI | | |
| DMO | | |
| HM-BME | | |
| TAE | | |
| p-TA | <0,01 | 0,4 ppm |
| Methanol | — | — |
| ITA | <0,01 | 2,4 ppm |
| OTA | <0,01 | 1,4 ppm |
| TA | 4699,8 | 99,996 |
| TAS | 0,07 | 16 ppm |
| Water | — | — |
| DME | — | — |
| MMT | 0,11 | 25 ppm |
| Σ Total | 4700,0 | 100,00 |

We claim:

1. A process for the production of a DMT intermediate product intended for working up to medium pure or pure dimethyl terephthalate (DMT) and/or medium pure or pure terephthalic acid (TA), the intermediate product having a total content of impurities of less than 1% by weight and a terephthalaldehydic acid methyl ester (TAE) content of less than 100 ppm, comprising:
   (a) jointly oxidizing a mixture containing predominantly para-xylene (p-X) and paratoluic acid methyl ester (p-TE) in the liquid phase with an oxygen-containing gas;
   (b) esterifying the acids produced in the oxidative step (a) with methanol;
   (c) distilling the reaction mixture produced in the esterification step (b) into:
      (I) a p-TE rich fraction,
      (II) a fraction containing more than 99% by weight DMT and its isomers, and
      (III) a high boiling residue fraction; and
   (d) recycling the p-TE fraction I to oxidation step (a), wherein the residue fraction III has a DMT content of 15 to 70% by weight and the DMT fraction II is purified by single solvent recrystallization to the DMT intermediate product such that the amounts of hydroxymethyl-benzoic acid methyl ester (HM-BME) and terephthalaldehydic acid methyl ester (TAE) amount together to less than 200 ppm in the DMT intermediate product.

2. A process according to claim 1, wherein the combined amounts of HM-BME and TAE in the DMT fraction II are less than 0.2% by weight, and the amounts of HM-BME and TAE in the DMT intermediate product are less than 50 ppm.

3. A process according to claim 1 wherein 3 to 7% by weight DMT, relative to the sum of all components supplied to oxidation step (a) in the liquid phase, is supplied additionally to oxidation step (a) together with the para-xylene and the p-TE fraction I.

4. A process according to claim 3, wherein the amount of DMT supplied additionally to the oxidation is obtained by working up residue fraction III.

5. A process according to claim 1, wherein, for the distillation of the esterification products, the ester mixture is separated in a first rectification column into a sump product forming the high boiling residue fraction III and a head product, with the pressure in the rectification column amounting to 0.15 to 0.5 bar at the sump and 0.1 to 0.4 bar at the head and the reflux ratio amounting to between 0.2 and 1, and the head product is split in the second rectification column into the DMT fraction II as sump product and the p-TE fraction I as head product, with the pressure in the second rectification column amounting to 0.2 to 0.7 bar at the sump and to 0.1 to 0.5 bar at the head and the reflux ratio amounting to between 0.5 and 2.5.

6. A process according to claim 2, wherein the combined amounts of H-BME and TAE in the DMT fraction II are less than 0.1% by weight.

7. A process according to claim 6, wherein 3 to 7% by weight DMT, relative to the sum of all components supplied to oxidation step (a) in the liquid phase, is supplied additionally to oxidation step (a) together with the para-xylene and the p-TE fraction I.

8. A process according to claim 7, wherein the amount of DMT supplied additionally to the oxidation is obtained from residue fraction III.

9. A process according to claim 8, wherein for the distillation of the esterification products, the ester mixture is separated in a first rectification column into a sump product forming in the high boiling residue fraction III and a head product, with the pressure in the rectification column amounting to 0.15 to 0.5 bar at the sump and 0.1 to 0.4 bar at the head and the reflux ratio amounting to between 0.2 and 1, and the head product is split in a second rectification column into the DMT fraction II as sump product and the p-TE fraction I as head product, with the pressure in the second rectification column amounting to 0.2 to 0.7 bar at the sump and to 0.1 to 0.5 bar at the head and the reflux ratio amounting to between 0.5 and 2.5.

* * * * *